(12) United States Patent
Bartig et al.

(10) Patent No.: US 6,408,213 B1
(45) Date of Patent: Jun. 18, 2002

(54) LOW PROFILE, VENTRICULAR, TRANSVENOUS, EPICARDIAL DEFIBRILLATION LEAD

(75) Inventors: Jeffrey T. Bartig, Maplewood; Stuart R. Chastain, Shoreview; Gwen Crevensten, Minneapolis; John E. Heil, White Bear Lake; Curtis C. Lindstrom, Roseville, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/407,364

(22) Filed: Sep. 29, 1999

(51) Int. Cl.⁷ .................................................. A61N 1/00
(52) U.S. Cl. ..................................................... 607/122
(58) Field of Search ................................ 607/116, 119, 607/122, 126, 128, 130, 129, 123; 600/374, 375, 381

(56) References Cited

U.S. PATENT DOCUMENTS

| | | | | |
|---|---|---|---|---|
| 3,974,834 A | * | 8/1976 | Kane | 128/418 |
| 5,545,206 A | * | 8/1996 | Carson | 607/126 |
| 5,755,766 A | * | 5/1998 | Chastain et al. | 607/122 |
| 5,759,202 A | * | 6/1998 | Schroeppel | 607/126 |
| 5,800,495 A | | 9/1998 | Machek et al. | |
| 5,800,497 A | * | 9/1998 | Bakels et al. | 607/122 |
| 5,803,928 A | * | 9/1998 | Tockman et al. | 607/122 |
| 5,931,864 A | * | 8/1999 | Chastain et al. | 607/128 |
| 6,001,085 A | * | 12/1999 | Lurie et al. | 604/282 |
| 6,070,104 A | * | 5/2000 | Hine et al. | 607/123 |
| 6,122,552 A | * | 9/2000 | Tockman et al. | 607/116 |
| 6,240,321 B1 | * | 5/2001 | Janke et al. | 607/122 |

FOREIGN PATENT DOCUMENTS

| | | |
|---|---|---|
| EP | 0 653 223 A2 | 10/1994 |
| WO | WO 99/55412 | 4/1999 |

* cited by examiner

Primary Examiner—Jeffrey R. Jastrzab
Assistant Examiner—Frances P. Oropeza
(74) Attorney, Agent, or Firm—Nikolai & Mersereau, P.A.

(57) ABSTRACT

A cardiac lead designed for implantation in the vasculature of the left side of the heart comprising a flexible lead body having a central lumen, a removable terminal pin, electrodes electrically coupled to the removable terminal pin, a mechanism for securing the electrodes in the proper position in the vasculature and a mechanism for sealing the central lumen after implantation to prevent body fluids from invading the lumen. The cardiac lead can be implanted or explanted using either a guidewire, a guide catheter or both.

13 Claims, 9 Drawing Sheets

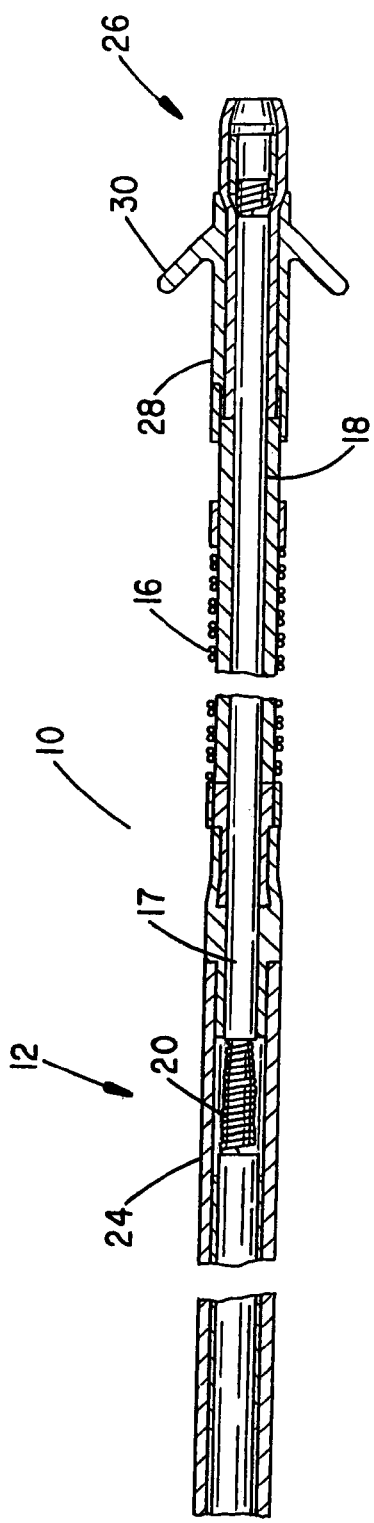
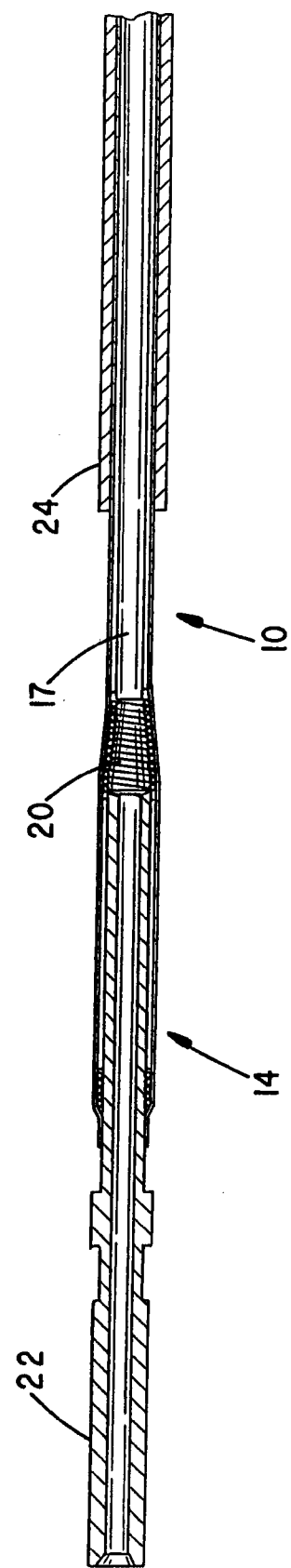
FIG. 2
FIG. 3

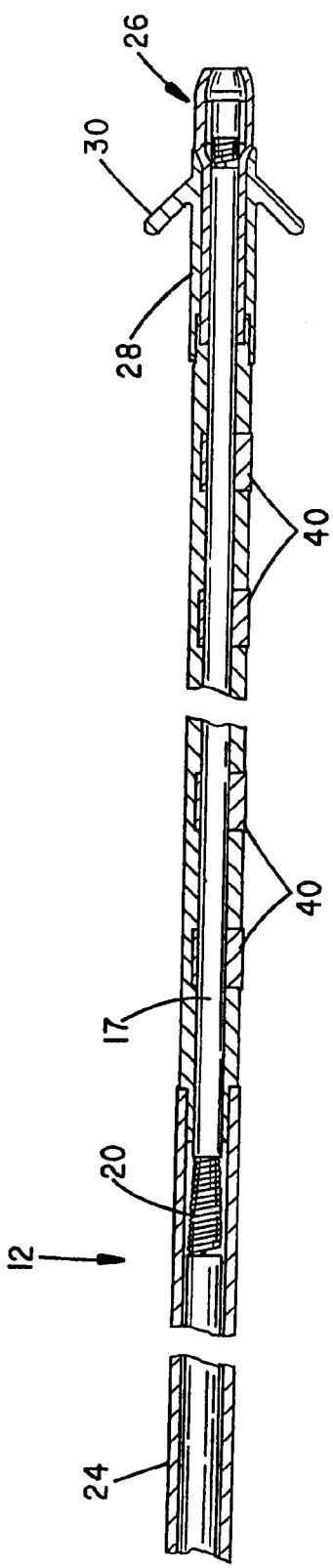
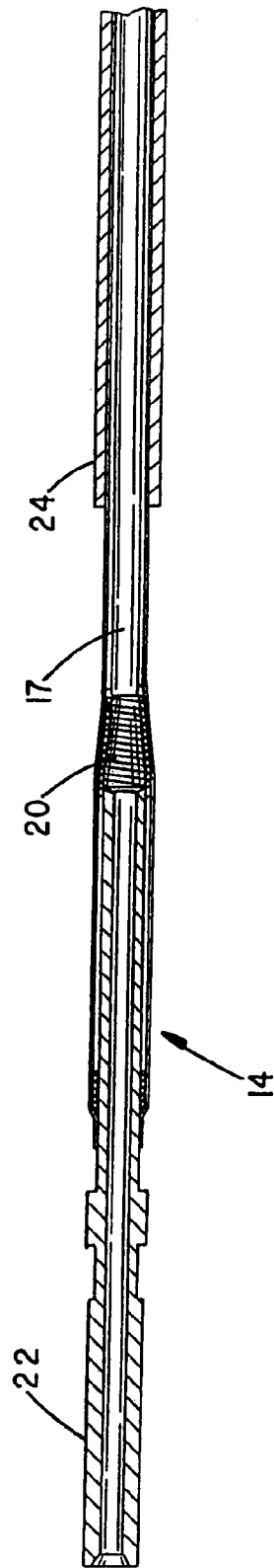
FIG. 5
FIG. 6

LOW PROFILE, VENTRICULAR, TRANSVENOUS, EPICARDIAL DEFIBRILLATION LEAD

BACKGROUND OF THE INVENTION

I. Field of the Invention

The present invention relates to implantable devices used to stimulate the heart to control the heart's rhythm. This invention is more specifically directed toward leads used to connect a pulse generator to the left side of the heart to provide defibrillating pulses to the heart.

II. Description of the Prior Art

As set forth in U.S. Pat. No. 5,803,928 granted on Sep. 8, 1998 to Tockman et al, important health benefits can be derived by positioning an electrode in a branch of the great vein of the heart to treat tachycardia. Others have discussed positioning an electrode in the vasculature of the left side of the heart to treat heart failure. The present invention contemplates placing an electrode there for purposes of defibrillation.

Not all leads are suitable for placement in the vasculature of the left side of the heart. Many leads have too great a diameter, are too inflexible, and include structures that do not permit the lead to be safely and easily advanced through the vasculature. Such problems are compounded when the lead must also be suitable for delivery of defibrillation pulses.

SUMMARY OF THE INVENTION

As indicated above, it is often advantageous to defibrillation therapy to the left ventricle of the heart. While it is possible to secure a defibrillation electrode to the exterior of the left ventricle, doing so involves cracking the chest wall and other highly invasive and traumatic surgical protocols. Much of this surgical trauma can be avoided through the use of a transvenous lead. Placing the lead in the left ventricle can increase the potential for clotting. Clear advantages can, therefore, be derived by placing the electrode in a branch of the coronary vein. However, for such a lead to be successfully implanted in this fashion for effective delivery of therapy to the ventricle, it must be of a design capable of meeting six critical needs.

First, such a lead must be designed so that one or more of its electrodes can be positioned in one of the coronary veins of the left side of the heart. As such, the distal end of the lead must follow a path which includes the right atrium, the coronary sinus and one of the coronary veins.

Second, the lead must include a suitable shocking electrode. To be suitable, the shocking electrode must be of a proper length, be sufficiently supported for both placement and explant, and yet flexible enough to travel through the venous structure.

Third, the lead must have an electrode capable of pacing and sensing. This may be accomplished using the same electrode used for shocking. Alternatively, separate electrodes on the lead can be used to perform the pacing and sensing functions.

Fourth, proper fixation of the lead is key. Once the electrode is properly positioned, it must remain in that position indefinitely. Changes in position can be caused by a variety of factors, including blood flow, if the lead is not properly fixed in place.

Fifth, if an "over-the-wire" type design is used, the open end of the lumen could be sealed once the guidewire is withdrawn. Otherwise undesirable flow of blood through the lumen of the lead might occur.

Finally, the terminal pins of the lead must be properly sized. They must be sized for coupling to the defibrillator. They also must permit removal of a guide catheter.

Leads constructed in accordance with the subject invention meet each of these six critical criteria through the incorporation of various specifically designed structures. First, leads of the present invention have a proximal section possessing adequate axial stiffness for torquing and pushing purposes. Such leads also have a flexible distal section for traversing the required path. The outer surface is coated with a lubricious material for ease of insertion. The tip is designed to be atraumatic to heart and vascular tissue. The lead is also designed to cooperate with a guidewire during the implantation process.

Second, the defibrillation electrode is sufficiently supported for placement and explant. The electrode is also properly sized and sufficiently flexible to travel through the venous structure. Once implanted, the electrode is capable of delivering adequate defibrillation pulses to the heart.

Third, sensing or pacing is performed either using the same electrode which delivers defibrillation pulses to the heart, or a separate electrode. If a separate electrode is used, it must have characteristics similar to the defibrillation electrode as discussed above and the lead body structure should have individually insulated conductive elements.

Fourth, any fixation device used to assure that the electrode is maintained in the proper position is designed to not interfere with efforts to place the electrode in the proper position. Thus, rather than impacting the cross-section of the lead during implantation, the fixation device either (a) biases in the lead body's conductive coil; (b) comprises one or more dissolvable polymers in the lead body to permit fibrotic attachment to the vein wall; or (c) has deployable tines. The fixation mechanism may also be made detachable to allow for explant of the lead.

Fifth, a guidewire will typically need to be used to position the electrode properly. If the lead has a distal opening and is passed over the guidewire, the distal opening is sealed once the electrode is properly positioned. In accordance with the present invention, this can be accomplished through the use of either a silicone flap, a hydrophilic material which swells upon fluid contact to close the distal opening, or the use of a deployable plug.

Finally, the terminal pins of the lead are designed to accommodate removal of a guide catheter. Either the terminal pins must be made small enough or the terminal pins must be removable.

More specifically, the present invention provides a lead suitable for both delivery of defibrillation pulses and placement in the vasculature of the heart. In one embodiment, a single lumen lead is provided. This lead includes an electrically conductive single open-lumen inner conductor coil comprising a winding of multiple wires to reduce electrical resistance. The coil is covered with an insulative material such as silicone, polytetrafluoroethylene (PTFE) or polyurethane. The proximal end is equipped with a terminal connector that can be plugged into the pulse generator. Just distal of the terminal connector is a self-sealing disk that permits passage of a guidewire and seals upon removal of the guidewire. Near the distal end of the lead are one or more electrodes specifically designed for flexibility and delivery of defibrillation pulses. The distal end, itself, includes a tip designed to be atraumatic and to dilate the venous structures to facilitate lead implantation. The lead may also include a fixation device for retaining the lead in the proper position.

Other embodiments of the invention provide a multi-lumen lead having one or more conductive cables passing through the lumens and attached to one or more electrodes. Again, a terminal connector for each cable, a self-sealing disk and an atraumatic tip are provided.

Further information related to the present invention and the advantages it offers can be derived from a review of the following detailed description of the invention in conjunction with the drawings which are a part of this specification. The specification is not intended to be limiting. Instead, the scope of the invention is defined by the claims when interpreted broadly to include a full range of equivalents.

BRIEF DESCRIPTION OF THE DRAWINGS

FIG. 2 cross-sectional view of the distal section of the lead shown in FIG. 1.

FIG. 3 is a cross-sectional view of the proximal section of the lead shown in FIG. 1.

FIG. 5 is a cross-sectional view of the distal section of the embodiment shown in FIG. 4.

FIG. 6 is a cross-sectional view of the proximal section of the embodiment shown in FIG. 4.

DETAILED DESCRIPTION OF THE PREFERRED EMBODIMENTS

Figure 1:
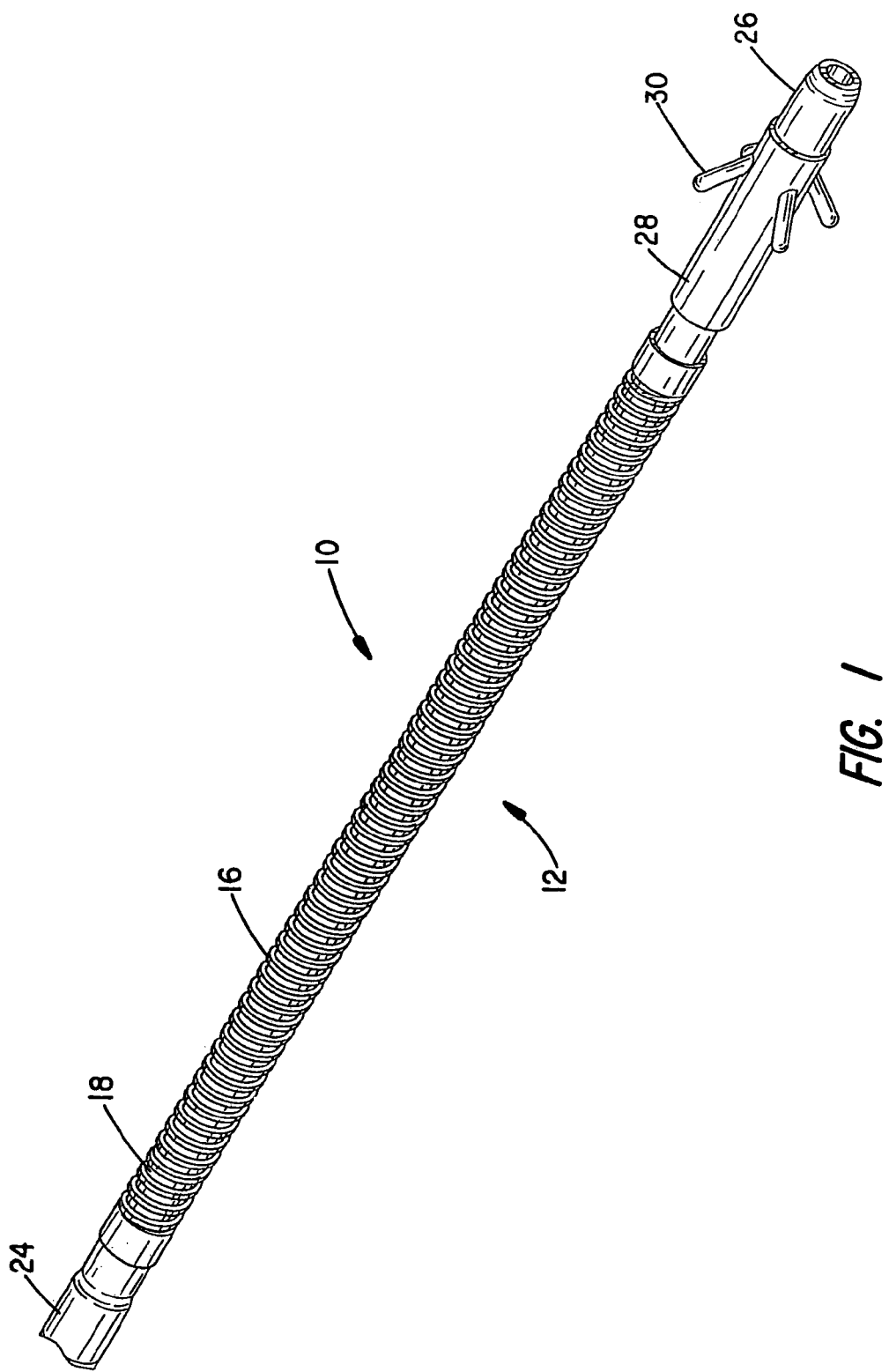
FIG. 1 is a perspective view showing the distal end section of the lead of the present invention.

A first embodiment of the invention is shown generally in FIGS. 1–3. The lead 10 includes a distal section 12 shown in FIGS. 1 and 2 and a proximal section 14 shown in FIG. 3. The distal section 12 includes a coil-shaped electrode 16. The electrode 16 can be made of a single wire. However, multi-filar wire coil is preferred. The coil-shaped electrode 16 surrounds a silicone tubing 18. The coil-shaped electrode 16 is also electrically coupled to a conductive coil 20 which is used to carry pulses between the electrode 16 and a terminal pin 22. The coil-shaped electrode 16 is preferably a winding of multiple wires coupled together. This also serves to significantly reduce electrical resistance. Suitable wire materials include platinum clad titanium, platinum clad tantalum, or platinum coated MP35N wire. The conductive coil 20 preferably has a biased area that can be used to help retain the lead in the desired position in the vein. The terminal pin 22 is used to couple the lead 10 to a cardiac rhythm management device such as an implantable defibrillator. The terminal pin 22 is preferably removable and/or small enough to permit the walls of a lumen of a guide catheter to pass over pin 22.

FIGS. 1–3 show other important features of the invention. For example, an insulative layer 24 surrounds the conductive coil 20. Suitable materials for the insulative layer 24 include silicone, polytetrafluoroethylene (PTFE) and polyurethane. Silicone offers the advantages of being very flexible and soft. PTFE offers the advantages of being thin, durable, and reduces abrasion. Polyurethane is stiffer than silicone, but smoother and more durable. The insulative layer 24 may include a combination of these materials. For example, the majority of the insulative layer might be silicone. A layer of PTFE might be placed between the coil 20 and the silicone on approximately two-thirds the length of the lead 10 to stiffen the proximal section to facilitate advancing the lead 10 over a guidewire during insertion of the lead. Polyurethane might be used as an outer layer over the silicone to prevent abrasion of the vessel wall as the lead is implanted a coating of a lubricious material may also be provided. Ideally, the proximal end section will be stiffer than the distal section so that the proximal section has sufficient axial stiffness to allow the lead to be advanced and the distal section is sufficiently flexible to be routed along the desired path and at the same time be sufficiently atraumatic.

FIGS. 1 and 2 show that the distal section 12 terminates with an atraumatic tip 26 at the distal end. The tip 26 is designed to completely cover the electrically conductive coil 20 to prevent vessel erosion. The tip 26 also acts to dilate the venous structure to facilitate implantation of the lead 10. Suitable materials for the tip 26 include silicone or other soft, pliable polymers.

FIGS. 1 and 2 also show a fixation device 28 incorporating a plurality of tines 30. These tines 30 are preferably deployable and act to increase the mechanical pressure against the vessel wall to hold the lead 10 in place. Suitable materials include silicone and polyurethane. The lead could be microtextured to permit fibrotic attachment to the wall of the coronary vein. The tines could also be made detachable or absorbable in the event the lead needs to be explanted. Materials could include poliglecaprone 25, polyglactin 910 or polydioxanone.

Figure 4:
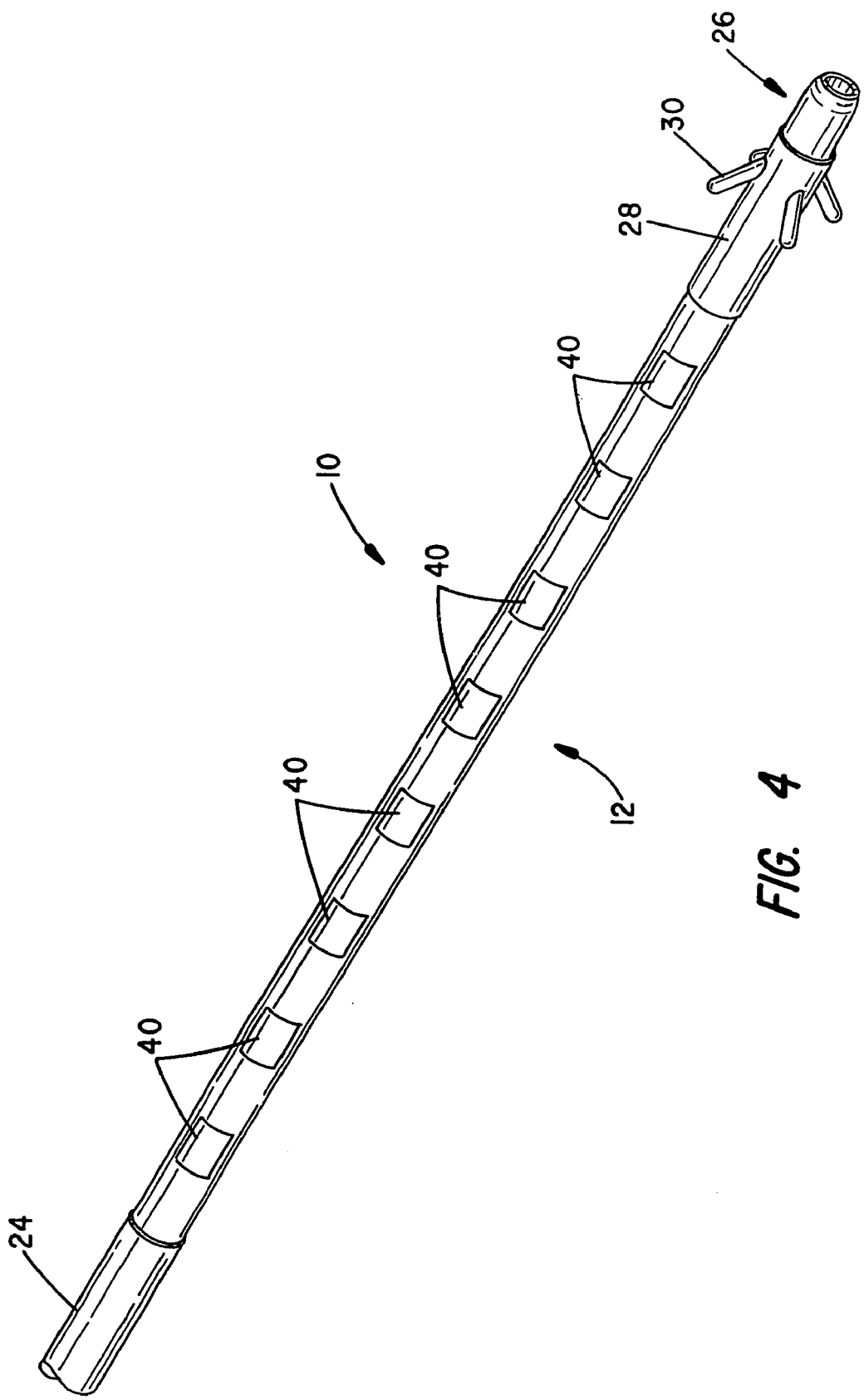
FIG. 4 is a perspective view of the distal section of a second embodiment of the present invention.

FIGS. 4–6 show an alternative embodiment of the present invention. This embodiment incorporates a plurality of small ring electrodes 40 in place of the wire coil electrode 16. A soft, flexible, insulative material covers the conductive coil 20 between the ring electrodes. The conductive coil 20, of course, carries current from the terminal pin 22 to each ring electrode. A plurality of cables could be used in place of the coil 20 if it is desired to have the ring electrodes 40 perform separate functions, i.e., pacing, defibrillating or sensing.

Figure 7:
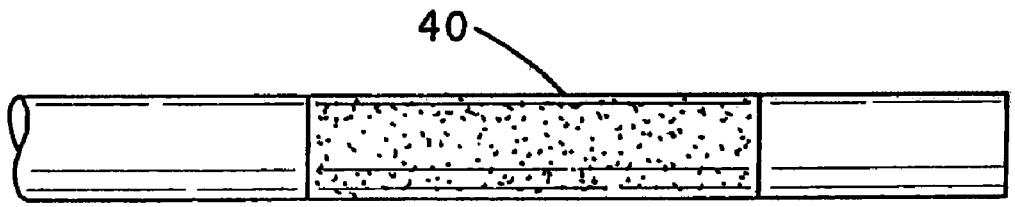
FIG. 7 is a side view showing a first electrode design.
Figure 8:
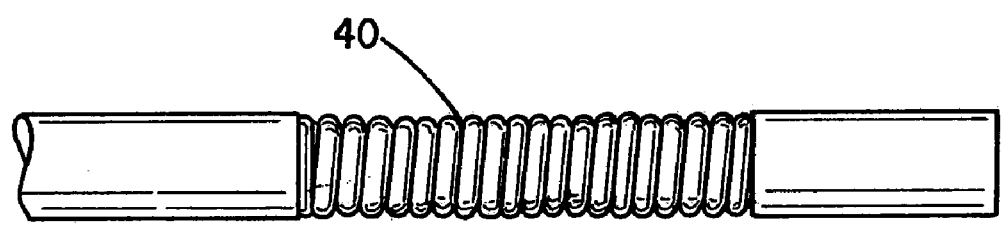
FIG. 8 is a side view showing a second electrode design.
Figure 9:
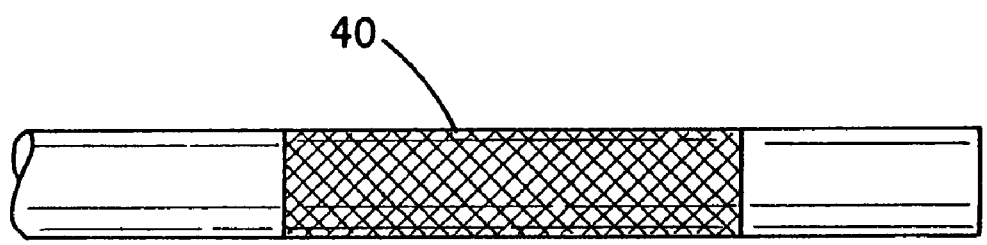
FIG. 9 is a side view showing a third electrode design.

FIGS. 7–9 show various alternative electrode designs. In FIG. 7, the electrode 40 comprises silicone rubber doped with conductive particles. In FIG. 8, the electrode 40 merely comprises an exposed section of the conductive coil 20. In FIG. 9 the electrode 40 is a conductive braided wire screen electrically coupled to the conductive coil 20. Of course, a standard ring electrode might also be used, but it would be less flexible than the electrode arrangements shown in FIGS. 7–9.

Figure 10:
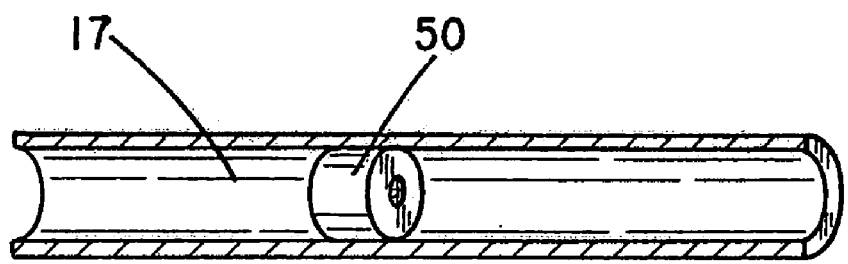
FIG. 10 is a side view of a self-sealing disk used to seal a lumen of the lead.
Figure 11:
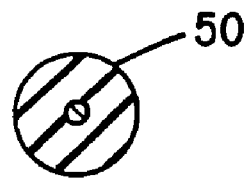
FIG. 11 is an end view of the self-sealing disk shown in FIG. 10.

A significant feature of the present invention is a deployable plug comprising the sealing disk 50 shown in FIGS. 10 and 11. This disk 50 is deployable so that it resides in the lumen 17 of the lead 10 to block the unintended passage of fluids through the lumen. The disk 50 is made of a low durometer silicone and has an orifice 52 that extends through it. The orifice 52 is sized to allow a guidewire to pass through it. However, when the guidewire is removed, the orifice seals behind it. Alternatively, the disk 50 could have a self-sealing flap or made of a hydrophilic material designed to expand when subjected to moisture to seal the lumen.

Figure 12:
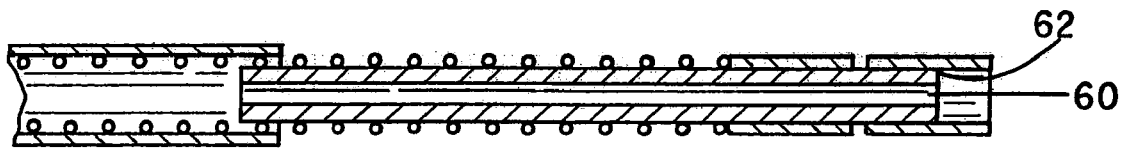
FIGS. 12–16 are each cross-sectional views showing alternative multi-lumen lead designs.
Figure 13:
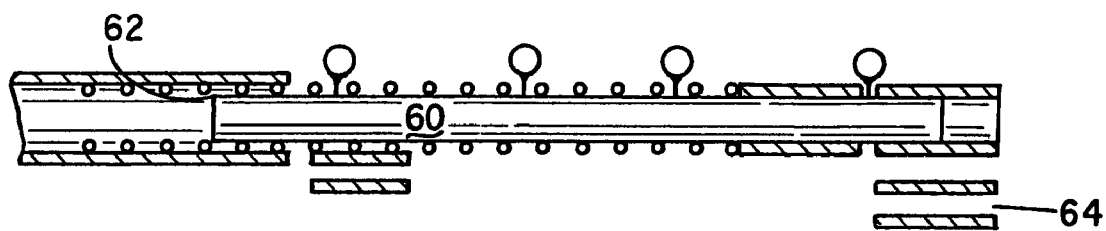

The present invention is not limited to a single lumen lead design. FIGS. 12–16 show separate multi-lumen designs fully within the scope of the invention. FIG. 12 shows a pair of concentric lumens 60 and 62. Lumen 60 is designed to accommodate a guidewire. A conductive cable resides in lumen 62. FIG. 13 shows a pair of concentric lumens 60 and 62 and a third lumen 64 that functions as a guide tube.

Figure 14:
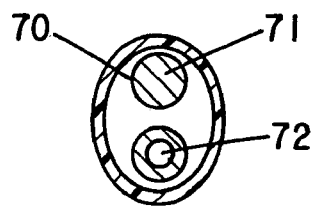
Figure 15:
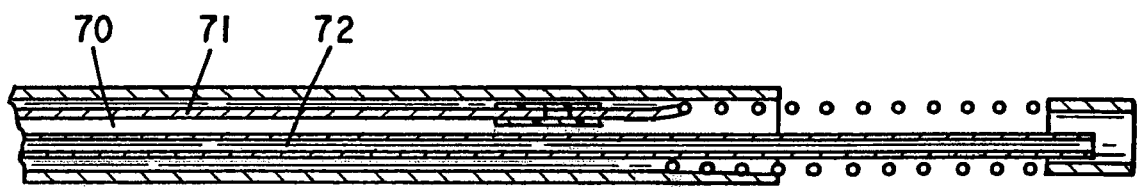
Figure 16:
Figure 17:
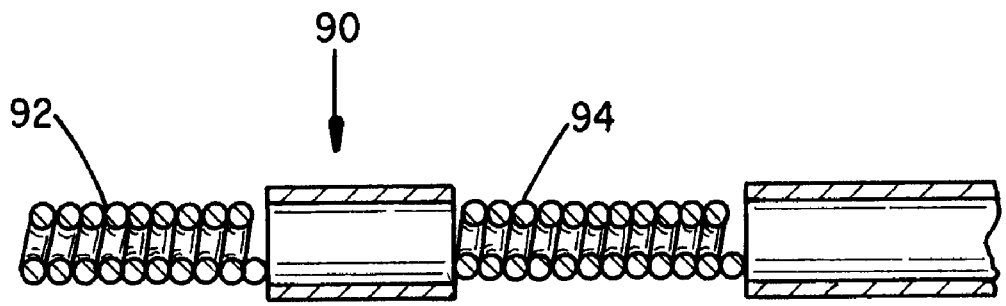
FIG. 17 shows a first embodiment of a dual in-line connector.
Figure 18:
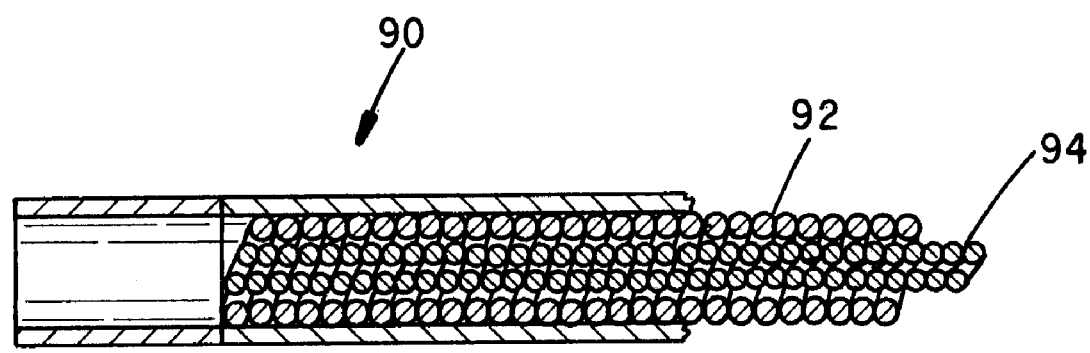
FIG. 18 shows a second embodiment of a dual in-line connector.

FIGS. 14 and 15 show a design that includes a first lumen 70 through which a cable conductor 71 passes and a lumen 72 to accommodate a guidewire, injection of fluoroscopic dye or the like. Finally, FIG. 16 shows an arrangement incorporating a larger central lumen 80 and smaller top and bottom lumens 82 and 84. The top lumen 82 can each include a braided cable 71 which replaces the conductive coil. The larger central lumen 80 can accommodate a guidewire. This lumen may be coated with a lubricious material so that the lead slides easily with respect to a guide wire used during implantation of the lead. The outer wall of the lead body can also be coated with a lubricious material to reduce friction between the lead and vessel wall. The bottom lumen can be used for dye injection or for another braided cable if the lead includes multiple electrodes used for differing purposes. When two such cables are provided, two terminal pins 22 or a dual in-line connector will be required. The first cable can be coupled to an electrode for delivery of defibrillating pulses. The second cable can be coupled to a second electrode for delivering pacing pulses to the heart or to sense the electrical activity of the heart. Alternatively, a dual in-line connector 90 of the types shown in either FIGS. 17 and 18 could be used. Each dual in-line connector has a first conductive element 92 and a second conductive element 94. In FIG. 17, the first and second conductive elements are spaced apart bands electrically insulated from each other. Each band is electrically coupled to a separate electrode by a wire or the like. In FIG. 18, the electrically conductive elements are a pair of coaxial wire coils, one having a smaller diameter than the other. Of course, other multiple arrangements can be used without deviating from the invention.

What is claimed is:

1. For use with a cardiac rhythm management device, a low profile, ventricular, transvenous, epicardial lead having:

(a) an elongated, flexible body member made of an electrically insulative material, said body member having a proximal section, a distal section, an outer wall extending the length of the body member, an opening through said outer wall in said distal section and a lumen extending from said opening through said outer wall, said proximal section being stiffer than the distal section, said proximal section possessing adequate axial stiffness and said distal section being sized and sufficiently flexible to permit the distal section to be advanced through the right atrium and coronary sinus into the coronary vein;

(b) an electrode capable of delivering defibrillating pulses to the left ventricle of the heart and coupled to the distal section of said body member, said electrode being of a size and flexibility to be advanced along with the distal section of the body member through the right atrium and coronary sinus into the coronary veins to a location adjacent the wall of the left ventricle;

(c) a terminal pin;

(d) a conductive member extending within said body member from said electrode for providing an electrical path between said electrode and said terminal pin;

(e) means for retaining said electrode in the coronary vein; and (f) a sealing disk made of a low durometer material with a self-sealing orifice capable of receiving a guidewire for sealing said opening through the outer wall of said body member.

2. The lead of claim 1 wherein said terminal pin can be detached and reattached with respect to the remainder of the lead.

3. The lead of claim 1 wherein said terminal pin is sufficiently small to permit the lumen of a guide catheter to pass over it.

4. The lead of claim 1 wherein said conductive member is a conductive coil and said means for retaining said electrode in the coronary vein includes biased areas in the conductive coil.

5. The lead of claim 1 wherein said means for retaining said electrode in said coronary vein includes at least one area of the body member incorporating microtexturing to permit fibrotic attachment to the wall of coronary vein.

6. The lead of claim 1 wherein said means for retaining said electrode in said coronary vein includes deployable tines.

7. The lead of claim 1 wherein said means for retaining said electrode in said coronary vein is detachable from the lead body to permit the lead body to be explanted.

8. The apparatus of claim 1 further including a second electrode, a second terminal pin and a second conductive member extending within said body member between said second electrode and said second terminal pin.

9. The apparatus of claim 1 wherein the outer wall of said lead body is coated with a lubricious material.

10. The apparatus of claim 1 wherein said lumen is coated with a lubricious material.

11. The apparatus of claim 1 wherein said distal section terminates in a soft tip which is atramatic to the heart tissue.

12. The apparatus of claim 1 wherein said means for retaining said electrode in the coronary vein incorporates a polymer which is dissolvable for explantation of the lead.

13. The apparatus of claim 1 wherein said terminal pin is a dual in-line terminal pin and further including a second electrode and a second conductive member extending within said body member from said second electrode or providing a second electrical path between said second electrode and said dual in-line terminal pin.

* * * * *

UNITED STATES PATENT AND TRADEMARK OFFICE
CERTIFICATE OF CORRECTION

PATENT NO.    : 6,408,213 B1
DATED         : June 18, 2002
INVENTOR(S)   : Jeffrey T. Bartig et al.

It is certified that error appears in the above-identified patent and that said Letters Patent is hereby corrected as shown below:

<u>Title page,</u>
Item [75], should read -- [75] Inventors: Jeffrey T. Bartig, Maplewood; Stuart R. Chastain, Shoreview; Gwen Crevensten, Minneapolis; John E. Heil, White Bear Lake; Curtis C. Lindstrom, Roseville, all of MN (US); Aaron W. Janke, Houston, TX. --

Signed and Sealed this

Fifteenth Day of October, 2002

*Attest:*

*Attesting Officer*

JAMES E. ROGAN
*Director of the United States Patent and Trademark Office*